United States Patent [19]

Lill et al.

[11] 4,409,334

[45] Oct. 11, 1983

[54] STABILIZED THROMBIN PREPARATION

[75] Inventors: Helmut Lill, Wielenbach; Knut Bartl, Wilzhofen, both of Fed. Rep. of Germany

[73] Assignee: Boehringer Mannheim GmbH, Mannheim-Waldhof, Fed. Rep. of Germany

[21] Appl. No.: 254,364

[22] Filed: Apr. 15, 1981

[30] Foreign Application Priority Data

May 22, 1980 [DE] Fed. Rep. of Germany ....... 3019612

[51] Int. Cl.$^3$ ...................... G01N 33/48; C09K 3/00
[52] U.S. Cl. ......................................... 436/8; 436/15; 436/69
[58] Field of Search ................. 252/408, 408.1; 435/4, 435/13; 436/8, 15, 69, 86

[56] References Cited

U.S. PATENT DOCUMENTS

| | | | |
|---|---|---|---|
| 3,931,399 | 1/1976 | Bohn et al. | 424/105 |
| 4,195,072 | 3/1980 | Workman, Jr. | 424/1 |
| 4,234,682 | 11/1980 | Bartl et al. | 435/13 |
| 4,301,028 | 11/1981 | Bartl et al. | 252/408 |

*Primary Examiner*—Benjamin R. Padgett
*Assistant Examiner*—M. Moskowitz
*Attorney, Agent, or Firm*—Felfe & Lynch

[57] ABSTRACT

The present invention provides a stabilized thrombin preparation in solid or dissolved form, especially for analytical purposes, containing, as a stabilizer, serum albumin together with at least one protease inhibitor and at least one chelate former.

8 Claims, No Drawings

STABILIZED THROMBIN PREPARATION

This invention related to a stabilized thrombin preparation. This preparation may be in solid or dissolved form and is especially suitable for diagnostic purposes.

Thrombin (blood coagulation Factor IIa) plays an important role in the process of blood coagulation. On the one hand, it acts back upon prothrombin (Factor II) in the sense of regulating the coagulation process but, in particular, it brings about the conversion of fibrinogen (Factor I) into fibrin monomer (FS), with the splitting off of peptide, which can be coagulated to give fibrin polymer. Therefore, thrombin plays an important role, especially in the diagnosis of the blood coagulation process. Thus, for example, it can be used for the determination of heparin or of antithrombin III.

The use of thrombin for investigations of the blood coagulation process and especially in test systems which are intended for this purpose, is considerably impaired by the extraordinarily great instability of thrombin, the instability being especially marked in dissolved form. Thus, for example, an aqueous solution of thrombin at 0° C. is only stable for about 5 hours (see Thromb. Diath. Hemorrh., 9, 169/1963). For some preparations, the stability in dissolved form at 0° C. is said to be only 1 hour.

Apart from this general instability of thrombin, it has been found that sometimes extraordinarily rapid and very marked changes of activity take place in the sense of an inactivation in the case of thrombin which, in the case of use in analytical tests, leads to completely useless results. Experiments have given rise to the view that this change of activity is due to the container surfaces with which the thrombin solution comes into contact.

It is, therefore, an object of the present invention to overcome these difficulties associated with the use of thrombin and to provide a stabilised thrombin preparation which, not only in solid but also in dissolved form, has a period of usefulness which is sufficient for practical purposes, unexpected time-independent changes of activity also being avoided.

Thus, according to the present invention, there is provided a stabilized thrombin preparation in solid or dissolved form, especially for analytical purposes, wherein, as stabilizer, it contains serum albumin, together with at least one protease inhibitor and at least one chelate former.

The present invention is based upon the observation that the three components of the stabilizer used according to the present invention exert a synergistic effectiveness which gives rise to a very stable thrombin preparation in which the previously observed phenomenon of a sudden decrease of activity does not occur. Thus, a stabilized thrombin preparation according to the present invention in the form of an aqueous solution, after storage for one month at 33° C., still has an activity which is about 80% of the initial value. If an aqueous solution of the preparation according to the present invention is stored in the usual manner at about 0° C., then for several months it only displays an insignificant change of activity.

The stabilised thrombin preparation according to the present invention preferably contains the chelate former in an amount of from 0.01 to 0.2 M, the protease inhibitor in an amount of from 1 to 100 $\mu$g./ml. and the serum albumin in an amount of from 5 to 100 mg./ml. or, if it is a dry preparation, in an amount which, upon dissolving in the intended amount of solvent, gives such concentrations.

Amongst the chelate formers, the hexaligands are preferred. Examples thereof include nitrilotriacetic acid, cyclohexene-(1,2)-dinitrilotetraacetic acid, diethylenetriaminepentaacetic acid and ethylenediaminetetraacetic acid (EDTA), EDTA being preferred. The best results are obtained when the chelate former is present in a concentration of from 0.03 to 0.1 M.

In the stabilized thrombin preparation according to the present invention, those protease inhibitors are used which do not inhibit thrombin itself, examples thereof including aprotinin and soya bean trypsin inhibitor (STi). Other protease inhibitors which can be used are mentioned in "The Enzymes", Vol.III, 3rd ed., 1971, pp. 380-382. Aprotinin is preferably used since it is readily available as a commercial preparation.

The third component of the stabilising agent contained in the thrombin preparation according to the present invention is serum albumin. The serum albumin can be of any desired origin but bovine serum albumin (BSA) is preferred because of its ready availability. As already mentioned, the solution preferably contains 0.5 to 10% and more preferably 1 to 5% (10 to 50 mg./ml.) of serum albumin. According to the results available, the serum albumin in particular prevents the sudden decrease of activity of the thrombin. It is assumed that this decrease of activity is caused by traces of detergent and especially by traces of anionic detergent which remain behind when cleaning apparatus and containers with which the thrombin solution comes into contact.

The stabilized thrombin preparation according to the present invention can be present as such or in admixture with other substances in the form of a combined reagent mixture. When it is present in dissolved form, then an approximately neutral pH value (6.0 to 8.0 and preferably 6.5 to 7.5) should be present. In most cases, the buffer capacity of the chelate former suffices in order to give this pH range. However, a conventional buffer substance can also be added. The dry preparation, which is generally present in lyophilised form, can also already contain such a buffer substance.

In the case of commercially available thrombin preparations, on average the activity in the case of storage in aqueous solution at ambient temperature decreases by about 50% in two weeks. Under the same conditions, in the case of a preparation stabilized according to the present invention, no decrease in activity occurs, within the limits of error.

The following Examples are given for the purpose of illustrating the present invention:

EXAMPLE 1

117 mg. of a stabilized thrombin lyophilisate comprising, by weight, 47.9% EDTA, 51.28% BSA, 0.02% aprotonin, 0.5% sodium azide (as preservation agent) and 0.3% thrombin, are dissolved in 3 ml. double distilled water and the stability of the solution is investigated. The results obtained are set out in the following Table:

TABLE 1

| | thrombin activity (pH 8.1; 25° C.); TOS—Gly—Pro—Arg—pNA as substrate | | |
|---|---|---|---|
| | initial activity (U/ml.) | 1 week (U/ml.) | 2 weeks (U/ml.) |
| lyophilisate stored | 0.46 | 0.46 | 0.48 |

TABLE 1-continued

| | thrombin activity (pH 8.1; 25° C.); TOS—Gly—Pro—Arg—pNA as substrate | | |
|---|---|---|---|
| | initial activity (U/ml.) | 1 week (U/ml.) | 2 weeks (U/ml.) |
| at +4° C.; solution stored at +4° C. | | | |
| lyophilisate stored at +4° C.; solution stored at ambient temperature | 0.47 | 0.46 | 0.48 |
| lyophilisate stored for 3 weeks at 35° C.; solution stored at +4° C. | 0.46 | 0.46 | 0.47 |
| lyophilisate stored for 3 weeks at 35° C.; solution stored at ambient temperature | 0.47 | 0.46 | 0.47 |

EXAMPLE 2

The stabilizing effectiveness of the stabilised thrombin preparation according to the present invention was compared with the stabilizing effectiveness of the individual components and of the various possible combinations of two of the three components present according to the present invention.

The following Table gives the decrease of the thrombin activity in percentages in the case of the various stabilized preparations. The amount of EDTA was 50 mM, pH 6.9; the amount of aprotonin was 1 mg./100 ml. and the amount of BSA was 2 g./100 ml.

TABLE II

| | Influence of EDTA, aprotonin and serum albumin on the thrombin stability | | | | | | | |
|---|---|---|---|---|---|---|---|---|
| storage at 35° C. (weeks) | double dist. water | BSA | aprotonin | aprotonin BSA | EDTA | EDTA aprotonin | EDTA BSA | EDTA aprotonin BSA |
| 1 | 87.5 | 85.7 | 65.8 | 82.2 | 17.0 | 10.6 | 10.0 | 8.3 |
| 2 | 98.0 | 98.0 | 89.5 | 95.6 | 31.9 | 12.8 | 12.0 | 10.4 |

From the above-given results, it can be seen that serum albumin does not exert any stabilizing influence, the protease inhibitor only exerts a very small stabilizing influence and the combination of serum albumin/protease inhibitor also does not stabilise at all. The chelate former admittedly stabilises but, by the addition of the mixture of serum albumin and protease inhibitor, which alone is completely ineffective, a considerably superior stabilizing action is achieved.

It will be understood that the specification and examples are illustrated but not limitative of the present invention and that other embodiments within the spirit and scope of the invention will suggest themselves to those skilled in the art.

We claim:

1. Stabilized thrombin preparation comprising thrombin and as a stabilizer serum albumin together with at least one protease inhibitor which does not inhibit thrombin itself and at least one tetraligand or hexaligand chelate former.

2. Stabilized thrombin preparation as claimed in claim 1, in solid form.

3. Stabilized thrombin preparation as claimed in claim 1 in dissolved form.

4. Stabilized thrombin preparation as claimed in claim 1 containing 0.01 to 0.2 M chelate former, 1 to 100 μg./ml. protease inhibitor and 5 to 100 mg./ml. serum albumin.

5. Stabilized thrombin preparation as claimed in claim 1, wherein the chelate former is a hexaligand.

6. Stabilized thrombin preparation as claimed in claim 5, wherein the hexaligand is ethylenediamine-tetraacetic acid.

7. Stabilized thrombin prepeparation as claimed in claim 1, wherein the protease inhibitor is aprotonin.

8. Stabilized thrombin preparation as claimed in claim 1 containing 0.03 to 0.1 M ethylenediamine-tetraacetic acid, 5 to 20 μg./ml. aprotonin and 10 to 50 mg./ml. serum albumin.

* * * * *